(12) United States Patent
Khajuria et al.

(10) Patent No.: US 6,593,127 B1
(45) Date of Patent: Jul. 15, 2003

(54) COMPOSITION FOR EARLY AND PROFUSE SPORULATION IN FUNGI AND A METHOD THEREOF

(75) Inventors: Rajinder Kumar Khajuria, Jammu (IN); Ram Vilas Parsad Sinha, Jammu (IN); Vijeshwar Verma, Jammu (IN); Ghulam Nabi Qazi, Jammu (IN); Sukhdev Swami Handa, Jammu (IN)

(73) Assignee: Council of Science and Industrial Research, New Delhi (IN)

( * ) Notice: Subject to any disclaimer, the term of this patent is extended or adjusted under 35 U.S.C. 154(b) by 0 days.

(21) Appl. No.: 10/067,132

(22) Filed: Feb. 4, 2002

(51) Int. Cl.⁷ .................................................. C12N 1/16
(52) U.S. Cl. .............................. 435/256.1; 435/256.7; 435/256.3; 435/256.8
(58) Field of Search ......................... 435/256.8, 256.1, 435/256.3, 256.7

(56) References Cited

U.S. PATENT DOCUMENTS 4,368,269 A * 1/1983 Staron ..................... 435/256.8
6,340,586 B1 * 1/2002 Sardaryan ................ 435/256.8

* cited by examiner

*Primary Examiner*—Herbert J. Lilling
(74) *Attorney, Agent, or Firm*—Ohlandt, Greeley, Ruggiero & Perle, L.L.P.

(57) ABSTRACT

The present invention relates to a composition useful for early and profuse sporulation in fungi with about 100 fold increase in spore count within 48 hours of inoculation, said composition comprising molasses ranging between 5–20 g/L, Corn Steep Liquor (CSL) ranging between 10–25 g/L, Sodium chloride (NaCl) ranging between 5–15 g/L, calcium sulphate ($CaSO_4$) ranging between 0.1–0.5 g/L, Potassium dihydrogen phosphate ($KH_2PO_4$) ranging between 0.001–0.01 g/L, Magnesium sulphate ($MgSO_4.7H_2O$) ranging between 0.001–0.01 g/L, Copper sulphate ($CuSO_4$) ranging between 0.001–0.0050 g/L, Ferrous sulphate ($FeSO_4$) ranging between 0.0009–0.005 g/L, an anti-foam agent, and optionally solidifying agent and a method thereof.

37 Claims, No Drawings

COMPOSITION FOR EARLY AND PROFUSE SPORULATION IN FUNGI AND A METHOD THEREOF

FIELD OF THE PRESENT INVENTION

The present invention relates to a composition useful for early and profuse sporulation in fungi with about 100 fold increase in spore count within 48 hours of inoculation, said composition comprising molasses ranging between 5–20 g/L, Corn Steep Liquor (CSL) ranging between 10–25 g/L, Sodium chloride (NaCl) ranging between 5–15 g/L, calcium sulphate ($CaSO_4$) ranging between 0.1–0.5 g/L, Potassium dihydrogen phosphate ($KH_2PO_4$) ranging between 0.001–0.01 g/L, Magnesium sulphate ($MgSO_4.7H_2O$) ranging between 0.001–0.01 g/L, Copper sulphate ($CuSO_4$) ranging between 0.001–0.0050 g/L, Ferrous sulphate ($FeSO_4$) ranging between 0.0009–0.005 g/L, an anti-foam agent, and optionally solidifying agent and a method thereof.

BACKGROUND AND PRIOR ART REFERENCES

Trichoderma species are used as efficient biocontrol agents against the soil-borne Wilt and Root-rot diseases of various crop plants. With the growing awareness of the harmful effects of many synthetic chemical pesticides on humans, non-target animals and plant species, and the environment as a whole, there has been a shift in attention to the research and development of more environment-friendly methods of pest and disease control.

Use of environmentally safe Disease Management Technologies based on Biopesticide and Biocontrol agents through natural enemies—parasitoids, predators and pathogens in integrated pest management programmes are ever increasing. Biocontrol agents like Trichoderma species and Gliocladium species are examples of some of the biocontrol agents used in the management of root diseases of chickpea, peas, groundnut, soybean spices and vegetables.

Root-rot diseases of crops in general and pulses in particular are a serious problem in rain-fed areas caused mostly by species of Fusarium and Rhizoctonia etc. Chemical control of these diseases requires a continuous use of fungicides, which is not economical and causes deleterious effects on the rhizosphere microflora and also have the residual problems.

WHO now has banned even some of the commonly used fungicides due to their severe toxicity. Under these circumstances the biocontrol agents can be used for the management of Root-rot diseases at comparatively cheaper cost with long term antagonistic effects against the pathogens because these biocontrol agents multiply and remain near the root zone of the plant giving protection to these plants throughout the growth period.

Investigations carried out world over have confirmed, that synthetic plant protection chemicals such as fungicides, insecticides and herbicides deteriorate soil fertility. Such deterioration occurs through disappearance of bio-diversity in soils. On account of this, several strains of soil microorganisms have been used which are able to suppress a wide range of disease causing microorganisms.

Jackson et al., (Enzyme-Microb. Technol.; (1991) 13, 6, 456–61) reported the culture media optimisation for production of the biological control agents *Gliocladium virens* G20, *Trichoderma pseudokoningii* IMI 322662, and *T. viride* IMI 322659 and IMI 322663. In glucose-alanine medium, the optimum dry wt./g carbon occurred with a C:N ratio of 15:1. Addition of 3.28-mg atoms iron/l to the medium increased biomass production of all isolates, but a concentration of 164-mg atoms/l was toxic to the Trichoderma species. Growth decreased in media lacking Mg, P, K or S, but the amount of the decrease differed between the four isolates. Sporulation in agar was reduced in the absence of Mg, P, K and N. Addition of biotin, p-amino -benzoic acid and thiamine-HCl increased biomass production slightly. The glucose-alanine basal medium supported better growth of all 4 isolates than a commercial molasses-yeast medium; conidia production was greater in the molasses-yeast medium. The pH of the glucose-alanine medium remained constant at 4.5, whereas the pH of the yeast-molasses medium (initially 5.5) increased to 8.0–8.6. Chlamydospores were produced by all isolates, but the numbers varied according to the culture conditions used.

Gervais and Sarrette (J.Fement.Bioeng. (1990, 69, 1, 46–50) reported the Emerson agar medium (18 g/l agar) containing sodium octanoate (1 g/l) as a 2-heptanone precursor and glycerol as a water activity depressor for the solid-state fermentation of *T. viride* for cheese aroma production. Cultures were grown in Petri dishes at 20° C. Sporulation was visible on the 9th day.

Toyama et al (J. Ferment. Technol.; (1983, 61, 4, 409–11) reported a sporulation medium for *T. reesei* QM 9414, to be used for the production of protoplasts. Kennedy-M-J; Davies-R-J; Surrey-M-R; Reader-S-L; Hoefakker-P-C, Australia's. Biotechnol; (1995) 5, 6, 349–54 reported preparation of biological control agents based on *Serratia entomophila, Bacillus thuringiensis*, Pestalotia species, *Truncatella augustata, Trichoderma viride*, Trichoderma species., cricket-paralysis virus, flock-house virus. The report focuses on the 4 areas of process expertise required to develop and produce a commercial biological control agent: (a) culture medium design, (b) scale-up of the biological production system, (c) downstream processing of the product and (d) extending the shelf life of the biological control agent.

Nigam P. (Process-Biochem.; (1994, 29, 5, 337–42) reported a medium containing diluted molasses solutions of 3–4% sugar concentration for *T. viride* QM 9414, *T. reesei* Rut-C-30 NRRL 11460 under submerged fermentation conditions (SF) performed in flasks in 100 ml medium with agitation at 180 rpm for 5 days.

Culture media for two-stage culture of *T. longibrachiatum, T. viride, T. aureoviride*, AN: 91-13819, CA: Moscow-Tech.Inst.Food-Ind. were reported. The culture medium (pH 4.0–4.2) used in stage I had the following composition (wt. %): wheat bran, 0.3–0.4; additional hydrolysed cotton cake, 0.3–0.4; gibbersib (sic) biomass, 0.45–0.50; $NH_4H_2PO_4$, 0.25–0.30; $K_2SO_4$, 0.20–0.22; and $MgSO_4$, 0.025–0.030. The culture medium used in stage 11 (pH 5.0–5.2) had the following composition (wt. %): beet-root pulp, 2.5–2.8; wheat bran, 0.3–0.4; additional hydrolysed cotton cake, 0.3–0.4; $K_2SO_4$, 0.25–0.30; $NH_4NO_3$, 0.25–0.30 and stomach contents hydrolyzate containing reducing compounds, 0.20–0.25.

Abou-Zeid (Bioresource-Technol.; (1991) 37, 3, 239–42) reported the following medium (pH 6) (g/l): cellulosic-source, 10.0; $(NH_4)_2SO_4$, 2.0; $KH_2PO_4$, 1.0; KCl, 0.5; $MgSO_4.7H_2O$, 0.5; $MnSO_4.4H_2O$, 0.05; and $FeSO_4.7H_2O$, 0.005, for the Fermentation of *T. viride* using leaflets and midribs of date palm (*Phoenix dactylifera*) leaves dried at 100–105° C., 144 hr at 30° C. with 200 rpm agitation. Pre-treatment of palm leaflets with 1% NaOH and 5% $H_2SO_4$ improved their suitability as C-sources for *T. viride* growth.

The conventional media reported earlier are based on expensive gradients such as yeast extract, malt extract, protein hydrolysates and the like. Such a media are not suited for the economic mass production of these biocontrol agents by fermentation at technical scales.

We have designed medium for the mass production of spores of Trichoderma species, a number of other sporulating ascomycetous fungi such as Aspergillus species, Penicillium species and other scantily sporulating species of fungi under solid state, surface and submerged fermentation conditions based on inexpensive agro-based industrial by-products like beet-root pulp, wheat bran, corn-steep liquor and molasses. These agro-waste industrial by products are rich in micro-nutrients and other essential elements like sugars, amino acids providing synergistic effects on the growth and sporulation of these fungi.

OBJECTS OF THE PRESENT INVENTION

The main object of the present invention is to develop a composition for early sporulation of the fungi.

Another main object of the present invention is to develop a composition for profuse sporulation of the fungi.

Yet another object of the present invention is to develop a composition for early and profuse sporulation in Trichoderma species, Aspergillus species, and Penicillium species.

Still another object of the present invention is to develop a composition for early and profuse sporulation in scantily sporulating fungi.

Still another object of the present invention is to develop a composition much more economical than commercially available compositions.

Still another object of the present invention is to develop a method for early and profuse sporulation in fungi.

Still another object of the present invention is to develop a method for sporulation under solid state, surface, or submerged fermentation conditions.

SUMMARY OF THE PRESENT INVENTION

The present invention relates to a composition useful for early and profuse sporulation in fungi with about 100 fold increase in spore count within 48 hours of inoculation, said composition comprising molasses ranging between 5–20 g/L, Corn Steep Liquor (CSL) ranging between 10–25 g/L, Sodium chloride (NaCl) ranging between 5–15 g/L, calcium sulphate ($CaSO_4$) ranging between 0.1–0.5 g/L, Potassium dihydrogen phosphate ($KH_2PO_4$) ranging between 0.001–0.01 g/L, Magnesium sulphate ($MgSO_4.7H_2O$) ranging between 0.001–0.01 g/L, Copper sulphate ($CuSO_4$) ranging between 0.001–0.0050 g/L, Ferrous sulphate ($FeSO_4$) ranging between 0.0009–0.005 g/L, an anti-foam agent, and optionally solidifying agent and a method thereof.

DETAILED DESCRIPTION OF THE PRESENT INVENTION

Accordingly, the present invention relates to a composition useful for early and profuse sporulation in fungi, said composition comprising molasses ranging between 5–20 g/L, Corn Steep Liquor (CSL) ranging between 10–25 g/L, Sodium chloride (NaCl) ranging between 5–15 g/L, calcium sulphate ($CaSO_4$) ranging between 0.1–0.5 g/L, Potassium dihydrogen phosphate ($KH_2PO_4$) ranging between 0.001–0.01 g/L, Magnesium sulphate ($MgSO_4.7H_2O$) ranging between 0.001–0.01 g/L, Copper sulphate ($CuSO_4$) ranging between 0.001–0.0050 g/L, Ferrous sulphate ($FeSO_4$) ranging between 0.0009–0.005 g/L, an anti-foam agent, and optionally solidifying agent.

In an embodiment of the present invention, said composition show most efficient sporulation with composition comprising molasses about 7.50 g/L, Corn Steep Liquor (CSL) about 20 g/L, Sodium chloride (NaCl) about 10 g/L, calcium sulphate ($CaSO_4$) about 0.25 g/L, Potassium dihydrogen phosphate ($KH_2PO_4$) about 0.0060 g/L, Magnesium sulphate ($MgSO_4.7H_2O$) about 0.0050 g/L, Copper sulphate ($CuSO_4$) about 0.0010 g/L, Ferrous sulphate ($FeSO_4$) about 0.0016 g/L, an anti-foam agent, and optionally solidifying agent.

In yet another embodiment of the present invention, using silicon oil as an anti-foam agent.

In still another embodiment of the present invention, silicon oil ranging between 0.1–0.5 ml.

In still another embodiment of the present invention, using agar as a solidifying agent.

In still another embodiment of the present invention, agar ranging between 5–25 g/L.

In still another embodiment of the present invention, said composition is effective with fungi selected from a group comprising Trichoderma species, Aspergillus species, and Penicillium species.

In still another embodiment of the present invention, said composition is effective with fungi Trichoderma species.

In still another embodiment of the present invention, said composition shows about 100-fold increase in spore count within 48 hours of inoculation.

In still another embodiment of the present invention, said composition shows average spore count ranging between $1-5 \times 10^8$ conidiospores/ml.

In still another embodiment of the present invention, said composition shows percentage viability of generated spores ranging between 90 to 100%.

In still another embodiment of the present invention, said composition is equally effective with scantily sporulating fungi.

In still another embodiment of the present invention, said composition is used for mass production of fungi of biocontrol activity.

In still another embodiment of the present invention, said composition is economical as compared to other commercially available compositions for same purpose.

In a further embodiment of the present invention a method for early and profuse sporulation in fungi with about 100 fold increase in spore count within 48 hours of inoculation, said method comprising:

In another embodiment of the present invention, inoculating about one week old spore culture of the fungi in a medium comprising molasses ranging between 5–20 g/L, Corn Steep Liquor (CSL) ranging between 10–25 g/L, Sodium chloride (NaCl) ranging between 5–15 g/L, calcium sulphate ($CaSO_4$) ranging between 0.1–0.5 g/L, Potassium dihydrogen phosphate ($KH_2PO_4$) ranging between 0.001–0.01 g/L, Magnesium sulphate ($MgSO_4.7H_2O$) ranging between 0.001–0.01 g/L, Copper sulphate ($CuSO_4$) ranging between 0.001–0.0050 g/L, Ferrous sulphate ($FeSO_4$) ranging between 0.0009–0.005 g/L, an anti-foam agent, and optionally solidifying agent, In yet another embodiment of the present invention, fermenting the inoculated culture at temperature about 27–30° C., and In still another embodiment of the present invention, obtaining large quantity of viable spores.

In still another embodiment of the present invention, inoculating said culture of step (a) with said spores of final concentration of about $1 \times 10^6$ conidia/ml.

In still another embodiment of the present invention, fermentation said culture of step (b) under solid state, surface, or submerged fermentation conditions.

In still another embodiment of the present invention, wherein rotating said inoculated culture in a rotor at rate of about 200 to 400 revolutions/minute.

In still another embodiment of the present invention, wherein agitating the said culture with said rotor at about 1.5–3.5 c.m. throw.

In still another embodiment of the present invention, wherein fermenting said culture with aeration rate of about 0.5–1.0 vvm.

In still another embodiment of the present invention, wherein fermenting said culture with pressure of about 07–1.4 psig.

In still another embodiment of the present invention, wherein spores of step (c) show viability ranging between 90 to 100%.

In still another embodiment of the present invention, wherein mixing said culture with a carrier in a ratio ranging between 1:2 to 2:1, to develop commercial formulation with biocontrol activity.

In still another embodiment of the present invention, wherein carrier used is lignite.

In still another embodiment of the present invention, said method show most efficient sporulation with composition comprising molasses about 7.50 g/L, Corn Steep Liquor (CSL) about 20 g/L, Sodium chloride (NaCl) about 10 g/L, calcium sulphate ($CaSO_4$) about 0.25 g/L, Potassium dihydrogen phosphate ($KH_2PO_4$) about 0.0060 g/L, Magnesium sulphate ($MgSO_4.7H_2O$) about 0.0050 g/L, Copper sulphate ($CuSO_4$) about 0.0010 g/L, Ferrous sulphate ($FeSO_4$) about 0.0016 g/L, an anti-foam agent, and optionally solidifying agent.

In still another embodiment of the present invention, said method shows duration of viability of spores of about 10–14 months at temperature of about 4° C. with carriers.

In still another embodiment of the present invention, said method shows duration of viability of spores of about 4–8 months at temperature of about 30° C. with carriers.

In still another embodiment of the present invention, said method shows average spore count ranging between $1-5\times10^8$ conidiospores/ml.

In still another embodiment of the present invention, development of a novel medium based on inexpensive agro-based industrial by-products like beet-root pulp, wheat bran, corn-steep liquor, molasses and some inorganic salts in a definite proportion useful for the production of viable spores of Trichoderma species (used as biocontrol agents) and a number of other sporulating ascomycetous fungi such as Aspergillus species, Penicillium species and other scantily sporulating species of fungi under solid state, surface and submerged fermentation conditions.

In still another embodiment of the present invention, conventional processes take 5–9 days for the production of 10 fold increase in the number of spores of Trichoderma species from the initial inoculum as against in the present novel medium wherein 100 fold increase in the number of spores is achieved in 48 hours.

In still another embodiment of the present invention, this therefore makes the present invented process an economical, fast and highly advantageous from the commercial viewpoint.

In still another embodiment of the present invention, ingredients based on agro-waste industrial by-products are high energy and protein rich natural sources containing large number of trace elements and are very often used in culture media. However, these ingredients have not been used for inducing early sporulation in ascomycetous fungi. These ingredients in the medium result in very fast and better sporulation under submerged fermentation conditions when compared to conventional medium (Molasses-yeast extract medium) containing yeast extract, peptone, malt extract and refined sugars like glucose, & sucrose.

In still another embodiment of the present invention, the above ingredients were dissolved in de-ionised water and steam sterilised at 121° C./15 lb for 15 min. The sterilisation of the medium is done ex-situ for the operation of small bench fermentors and in-situ when large vessels are operated.

In still another embodiment of the present invention, for initiation of the fermentation process, spores from the a week old culture of Trichoderma species raised on solid medium (FM1medium with agar) are eluted with pre-sterile Tween 80 solution (0.02% v/v in water) and inoculated in the fermentor to the final concentration of $1\times10^6$ conidia/ml.

In still another embodiment of the present invention, fermentation is carried out in FM1 medium in cylindrical glass jars or stainless steel vessels at 29±1° C.

In still another embodiment of the present invention, the vessels are agitated with standard stirrers at a moderate rate of 200–400 rpm and aerated at a constant air flow of 0.5 to 1.0 volumes per volume of liquid per minute at 1 bar (kg) over pressure.

In still another embodiment of the present invention, all the inoculated spores germinate and vegetative growth of the fungus with a numerous chlamydospores emerges within 24-h fermentation period.

In still another embodiment of the present invention, thereafter, sporulation sets in and chiamydospores disappear completely within next 24-h fermentation period.

In still another embodiment of the present invention, fermentation is terminated after an incubation period of 48–72 h or until the maximum conidiospore concentration of $1-5\times10^8$/ml is obtained and no chlamydospores are spotted under microscopic examination.

In still another embodiment of the present invention, whole culture broth is thereafter thoroughly mixed with pre-sterilised lignite (dry heated at 120° C. for 6–8 h. and later cooled to room temperature) of mesh size 200–250 in the ratio of 1:2 and packed in 200 g packets in milky white pollywogs (size 6"×10") of 50–75 µg thickness.

In still another embodiment of the present invention, the biocontrol formulation thus prepared can be stored at 4° C. for a period of 12 months and at 30° C. upto 6 months, without significant loss of viability.

It is surprising to notice sporulation of this exorbitant quantum in fungi and that too in such a short span of time. The said composition shows about 100-fold increase in spore count within 48 hours of inoculation. All the ingredients of the composition comprising molasses ranging between 5–20 g/L, Corn Steep Liquor (CSL) ranging between 10–25 g/L, Sodium chloride (NaCl) ranging between 5–15 g/L, calcium sulphate ($CaSO_4$) ranging between 0.1–0.5 g/L, Potassium dihydrogen phosphate ($KH_2PO_4$) ranging between 0.001–0.01 g/L, Magnesium sulphate ($MgSO_4.7H_2O$) ranging between 0.001–0.01 g/L, Copper sulphate ($CuSO_4$) ranging between 0.001–0.0050 g/L, Ferrous sulphate ($FeSO_4$) ranging between 0.0009–0.005 g/L, an anti-foam agent, and optionally solidifying agent, show synergy to bring about unexpected early and profuse sporulation.

The said ingredients and their quantum in said composition are critical. Any change in the ingredients or their quantity do not produce desired results. In one experiment, molasses was not added in the said composition and sporulation was observed with only about 5-fold increase. Similarly, not adding corn-steep liquor led to only about 4-fold increase in the sporulation. Also, when all the said ingredients of the said composition are added but with potassium dihydrogen phosphate at concentration higher then the above-mentioned range, sporulation was only about 2-fold. Similarly, higher then the above defined range of copper sulphate showing normal (normal means using conventional substrate) sporulation with no increase in sporulation at all.

All these observations prove that all the said ingredients and their concentration ranges are extremely critical for the desired results. Any deviation from the same severely affects the sporulation in fungi.

The Following examples are given by way of illustration and should not construe the scope of the invention.

EXAMPLES

Example 1

Production of Spores of Trichoderma Species in Shake Flasks using FM1 Medium.

Strains of Trichoderma species were obtained from culture repository of Indian Agriculture Research Institute New Delhi. The cultures are maintained on standard Potato-dextrose medium (Potatoes 300 (g/l), glucose 20 (g/l) agar 17 (g/l)). For the purpose of mass propagation of its spores, the culture is pre-grown for a week in test tubes or large suitable containers like Roux bottles on FM1 medium containing Molasses 7.50 (g/l), Corn Steep Liquor (CSL) 20.00 (g/l), Sodium chloride 10.00 (g/l), $CaSO_4$ 0.2500 (g/l), $KH_2PO_4$ 0.0060 (g/l), $MgSO_4.7\ H_2O$ 0.0050 (g/l), $CuSO_4$ 0.0010 (g/l), $FeSO_4$ 0.0016 (g/l) and additional Agar 15.00.

For the production of the spores of Trichoderma species at the shake flask scale, the culture is raised in an Erlenmeyer flask of 500 ml capacity containing 100 ml of above described FM1 medium without agar, autoclaved at 121° C./15 lb for 15 min. The medium was inoculated with the spores of Trichoderma species with final concentration of $1\times10^6$ conidia/ml from one week old slant eluted in pre-sterile Tween 80 (0.02% v/v in water) solution and incubated on rotary shaker agitated at 180 revolutions/minute and 2.5 cm throw at 30° C. for 4 days.

At the end of the fermentation time no vegetative cells or chlamydospores were seen under microscope. An average conidia count of $5\times10^8$/ml broth was obtained. The viability of spores as determined by colony forming units on standard Potato Dextrose Agar (PDA) was of the order of 95 to 100%. Spore count ($5\times10^8$/ml) is achieved in this novel medium is 100 times from the initial inoculum during the above incubation period.

On the other hand in conventional medium (Molasses-yeast extract medium containing Molasses 7.50 (g/l), Glycerin 7.50 (g/l), Sodium Chloride 10.00 (g/l), Yeast Extract 5.00 (g/l), $CaSO_4$ 0.25 (g/l), $KH_2PO_4$ 0.006 (g/l), $MgSO_4.7\ H_2O$ 0.005 (g/l), $CuSO_4$ 0.001 (g/l), and Trace Elements 0.0016 (g/l)), it is only five fold during the same period. Besides, the number of chlamydospores in the conventional medium is much higher at any given time as compared to the new medium. Chlamydospores are not considered useful for packaging the fungi and only the conidiospores are used for downstream processing due to the better viability of the latter. The higher number of Chlamydospores in the conventional medium (Molasses-yeast extract) make it much inferior compared to the designed novel medium (FM1).

The viable conidia thus generated under submerged conditions are mixed with pre-sterilised lignite of 200–250 mesh size by doing so the spores remain viable for 6–8 months at 30° C. This lignite carrier based spores of Trichoderma species preparation was field tested on several crops with satisfactory results.

Example 2

Production of Spores of Trichoderma Species in Shake Flasks using FM1 Medium with Higher Concentration of Ingredients.

The seed of spores of Trichoderma species was raised in Erlenmeyer flasks in FM1 medium (medium containing Molasses 7.50 (g/l), Corn Steep Liquor (CSL) 20.00 (g/l), Sodium chloride 10.00 (g/l), $CaSO_4$ 0.2500 (g/l), $KH_2PO_4$ 0.0060 (g/l), $MgSO_4.7\ H_2O$ 0.0050 (g/l), $CuSO_4$ 0.0010 (g/l), $FeSO_4$ 0.0016 (g/l)) as described in example 1.

For the production of spores of Trichoderma species at the shake flask scale, the culture is raised in an Erlenmeyer flask of 500 ml capacity containing 100 ml of FM1 medium with following ingredients Molasses 20.00 (g/l), Corn Steep Liquor (CSL) 25.00 (g/l), Sodium chloride 15.00 (g/l), $CaSO_4$ 0.500 (g/l), $KH_2PO_4$ 0.01 (g/l), $MgSO_4.7\ H_2O$ 0.01 (g/l) 0.0050 (g/l), $FeSO_4$ 0.005 (g/l)) without agar, autoclaved at 121° C./15 lb for 15 min.

The medium was inoculated with the spores of Trichoderma species with final concentration of $1\times10^6$ conidia/ml from one week old slant eluted in pre-sterile Tween 80 (0.02% v/v in water) solution and incubated on rotary shaker and agitated at 180 evolutions per minute and 2.5 cm throw at 30° C. for 4 days.

At the end of the fermentation time no vegetative cells or chlamydospores were seen under microscope. An average conidia count of $5\times10^8$/ml broth was obtained. The viability of spores as determined by colony forming units on standard Potato Dextrose Agar (PDA) was of the order of 92 to 100%.

In the FM1 medium (with higher concentrations of ingredients) spore count ($5\times10^8$/ml) is achieved which is also 100 times from the initial inoculum during the above incubation period as against the conventional medium (Molasses-yeast extract medium containing Molasses 7.50 (g/l), Glycerin 7.50 (g/l), Sodium Chloride 10.00 (g/l), Yeast Extract 5.00 (g/l), $CaSO_4$ 0.25 (g/l), $KH_2PO_4$ 0.006 (g/l), $MgSO_4.7\ H_2O$ 0.005 (g/l), $CuSO_4$ 0.001 (g/l), and Trace Elements 0.0016 (g/l)).

Only five-fold increase in the number of spores from the initial inoculum is achieved in the Molasses-yeast extract medium during the same incubation period. Besides, the number of chlamydospores in this medium is much higher at any given time as compared to the new medium.

However, the spore concentration per ml and incubation period remained the same in both FM1 medium with higher concentrations of ingredients and FM1 medium with lesser concentration of ingredients (medium containing Molasses 7.50 (g/l), Corn Steep Liquor (CSL) 20.00 (g/l), Sodium chloride 10.00 (g/l), $CaSO_4$ 0.2500 (g/l), $KH_2PO_4$ 0.0060 (g/l), $MgSO_4.7\ H_2O$ 0.0050 (g/l), $CuSO_4$ 0.0010 (g/l), $FeSO_4$ 0.0016 (g/l).

Example 3

Production of Spores of Trichoderma Species in 7 Liter Batch Fermentor using the FM1 Medium.

The seed was raised in Erlenmeyer flasks in FM1 medium (medium containing Molasses 7.50 (g/l), Corn Steep Liquor (CSL) 20.00 (g/l), Sodium chloride 10.00 (g/l), $CaSO_4$ 0.2500 (g/l), $KH_2PO_4$ 0.0060 (g/l), $MgSO_4.7\,H_2O$ 0.0050 (g/l), $CuSO_4$ 0.0010 (g/l), $FeSO_4$ 0.0016 (g/l) as described in example 1. 7 liters of FM1 medium (medium containing Molasses 7.50 (g/l), Corn Steep Liquor (CSL) 20.00 (g/l), Sodium chloride 10.00 (g/l), $CaSO_4$ 0.2500 (g/l), $KH_2PO_4$ 0.0060 (g/l), $MgSO_4.7\,H_2O$ 0.0050 (g/l), $CuSO_4$ 0.0010 (g/l), $FeSO_4$ 0.0016 (g/l) along with 3 ml of silicon oil as antifoam agent was sterilised in-situ in a 10 l fermentor (New Brunswick, USA) at 121° C./15 lb. for 15 min. The medium on cooling was inoculated with 100 ml of freshly grown seed culture with the final spores concentration of $2–3 \times 10^6$.

The fermentor was set with the following parameters:

| | |
|---|---|
| Agitation | = 250 rpm |
| Aeration rate | = 0.5 vvm |
| Temperature | = 29° C. ± I |
| Pressure | = 1.2 psig |

The fermentation was continued for 72 hours until the spore concentration of $1.0 \times 10^9$ was achieved (Table 1). Data of periodic sampling for spore counting at regular intervals of time using both FM1 and conventional medium (Molasses-yeast extract medium containing: Molasses 7.50 (g/l), Glycerin 7.50 (g/l), Sodium Chloride 10.00 (g/l), Yeast Extract 5.00 (g/l), $CaSO_4$ 0.25 (g/l), $KH_2PO_4$ 0.006 (g/l), $MgSO_4.7\,H_2O$ 0.005 (g/l), $CuSO_4$ 0.001 (g/l), and Trace Elements 0.0016 (g/l)) media are shown in the Tables 1&2.

TABLE 1

Growth and sporulation of Trichoderma species in 7L fermentor using novel FM1 medium

| Time (h) | Conidiospores/ml | Chlamydospores/ml | Dry biomass (g % w/v) |
|---|---|---|---|
| 0 | $2.0 \times 10^6$ | Nil | — |
| 12 | — | | 0.24 |
| 24 | $2.0 \times 10^7$ | $1.2 \times 10^3$ | 0.43 |
| 48 | $3.0 \times 10^8$ | — | 0.31 |

TABLE 2

Growth and sporulation of Trichoderma species in 7L fermentor using conventional (Molasses-yeast extract) medium

| Time (h) | Conidiospores/ml | Chlamydospores/ml | Dry biomass (g % w/v) |
|---|---|---|---|
| 0 | $2 \times 10^6$ | Nil | 0.05 |
| 24 | $0.25 \times 10^5$ | $4.75 \times 10^5$ | 0.44 |
| 48 | $7.5 \times 10^6$ | $9.15 \times 10^6$ | 0.45 |
| 72 | $1.05 \times 10^7$ | $1.05 \times 10^7$ | 0.50 |
| 96 | $0.95 \times 10^7$ | $0.72 \times 10^7$ | 0.45 |
| 120 | $2.0 \times 10^7$ | $1.0 \times 10^7$ | 0.45 |
| 144 | $5.0 \times 10^7$ | $0.7 \times 10^7$ | 0.35 |

This novel medium (FM1) reduces fermentation period from 72 hrs to 48 hrs for sporulation. Moreover spore count $(3.0 \times 10^8)$ is achieved in this novel medium which is 100 times from the initial inoculum in 48 hrs whereas in case of conventional medium (Molasses-yeast) it is less than 10 times $(1.05 \times 10^7)$ 72 hrs. Besides, number of chlamydospores in conventional medium is much higher as compared to the novel medium as any fixed time internal.

Example 4
Production of Spores of Trichoderma Species in 7 Liter Batch Fermentor using FM1 Medium with Higher Concentration of Ingredients.

The seed was raised in Erlenmeyer flasks in FM1 medium (medium containing Molasses 7.50 (g/l), Corn Steep Liquor (CSL) 20.00 (g/l), Sodium chloride 10.00 (g/l), $CaSO_4$ 0.2500 (g/l), $KH_2PO_4$ 0.0060 (g/l), $MgSO_4.7\,H_2O$ 0.0050 (g/l), $CuSO_4$ 0.0010 (g/l), $FeSO_4$ 0.0016 (g/l) as described in example 1. 7 liters of FM1 medium with following ingredients Molasses 20 (g/l), Corn Steep Liquor (CSL) 25.00 (g/l), Sodium chloride 15.00 (g/l), $CaSO_4$ 0.500 (g/l), $KH_2PO_4$ 0.01 (g/l), $MgSO_4.7\,H_2O$ 0.01 (g/l), $CuSO_4$ 0.0050 (g/l), $FeSO_4$ 0.005 (g/l) without agar, along with 3 ml of silicon oil as antifoam was sterilised in-situ in a 10 l fermentor (New Brunswick, USA) at 121° C./15 lb. for 15 min. The medium on cooling was inoculated with 100 ml of seed culture with the final spores concentration of $2–3 \times 10^6$.

| | |
|---|---|
| Agitation | = 250 rpm |
| Aeration rate | = 0.5 vvm |
| Temperature | = 29° C. ± I |
| Pressure | = 1.2 psig |

The fermentor was set with the following parameters:
The fermentation was continued for 72 hours until the spore concentration of $1.0 \times 10^9$ was achieved (Table 3). Data of periodic sampling for spore counting at regular intervals of time using both FM1 and conventional (Molasses-yeast extract medium containing Molasses 7.50 (g/l), Glycerin 7.50 (g/l), Sodium Chloride 10.00 (g/l), Yeast Extract 5.00 (g/l), $CaSO_4$ 0.25 (g/l), $KH_2PO_4$ 0.006 (g/l), $MgSO_4.7\,H_2O$ 0.005 (g/l), $CuSO_4$ 0.001 (g/l) and Trace Elements 0.0016 (g/l) media are shown in the Tables 3&4.

TABLE 3

Growth and sporulation of Trichoderma species in 7L fermentor using novel FM1 medium with higher concentration of ingredients

| Time (h) | Conidiospores/ml | Chlamydospores/ml | Dry biomass (g % w/v) |
|---|---|---|---|
| 0 | $2.0 \times 10^6$ | Nil | — |
| 12 | — | | 0.29 |
| 24 | $2.8 \times 10^7$ | $1.35 \times 10^3$ | 0.48 |
| 48 | $3.6 \times 10^8$ | — | 0.39 |

TABLE 4

Growth and sporulation of Trichoderma species in 7L fermentor using conventional (Molasses-yeast extract) medium

| Time (h) | Conidiospores/ml | Chlamydospores/ml | Dry biomass (g % w/v) |
|---|---|---|---|
| 0 | $2 \times 10^6$ | Nil | 0.05 |
| 24 | $0.29 \times 10^5$ | $4.85 \times 10^5$ | 0.49 |
| 48 | $7.9 \times 10^6$ | $9.25 \times 10^6$ | 0.50 |
| 72 | $1.15 \times 10^7$ | $1.15 \times 10^7$ | 0.60 |
| 96 | $1.00 \times 10^7$ | $0.92 \times 10^7$ | 0.40 |
| 120 | $2.2 \times 10^7$ | $1.2 \times 10^7$ | 0.44 |
| 144 | $5.15 \times 10^7$ | $0.9 \times 10^7$ | 0.30 |

Perusal of the fermentation data show that the spore concentration/ml and incubation period remained the same as in the FM1 medium with lesser concentration of ingredients (medium containing Molasses 7.50 (g/l), Corn Steep Liquor (CSL) 20.00 (g/l), Sodium chloride 10.00 (g/l), $CaSO_4$ 0.2500 (g/l), $KH_2PO_4$ 0.0060 (g/l), $MgSO_4.7\,H_2O$ 0.0050 (g/l), $CuSO_4$ 0.0010 (g/l), $FeSO_4$ 0.0016 (g/l).

Thus the novel medium (FM1) with lower concentrations of ingredients is more economical & reduces fermentation period from 72 hrs to 48 hrs for sporulation as compared to the conventional medium (Molasses-yeast extract).

Example 5
Production of Spores of Trichoderma Species in 50 Liter Pilot Fermentor using the FM1 Medium.

Spores of Trichoderma species raised in Roux bottles containing solid FM1 medium of the composition as described in Examples 1 &3 above were eluted in Tween 80 (0.02% in water). 50 liters of FM1 medium containing Molasses 7.50 (g/l), Corn Steep Liquor (CSL) 20.00 (g/l), Sodium chloride 10.00 (g/l), $CaSO_4$ 0.2500 (g/l), $KH2PO_4$ 0.0060 (g/l), $MgSO_4.7\ H_2O$ 0.0050 (g/l), $CuSO_4$ 0.0010 (g/l), $FeSO_4$ 0.0016 (g/l) as described in Examples 1 &3 along with 15–25 ml of silicon oil as antifoam (the amount of silicon oil varied depending upon development of foam during fermentation) was sterilised in-situ in the 100 l fermentor (Andel, India) at 121° C./15 psig for 15 min. The medium on cooling was inoculated with 450–550 ml of spore suspension in Tween 80 solution with the final spores concentration of $1\times10^6$/ml.

The fermentor was set with the following parameters:

| | |
|---|---|
| Agitation | = 250 rpm (revolutions per min.) |
| Aeration rate | = 0.5 vvm (volume per volume per min.) |
| Temperature | = 29° C. ± 1 |
| Pressure | = 1.2 psig (pounds per square inch × g) |

The fermentation was continued for 48 hours until the spore concentration of $2.3\times10^8$ was achieved (Table 5). Periodic sampling for spore counting was carried out at regular intervals of time as shown in the Table 5.

TABLE 5

Growth and sporulation of Trichoderma species in 50-L fermentor using new FM1 medium

| Fermentation Period (h) | Dry biomass (g/l) | Spore count/ml |
|---|---|---|
| 0 | 0.02 | $1.0 \times 10^6$ |
| 12 | 0.24 | — |
| 24 | 0.43 | $2.0 \times 10^5$ |
| 30 | 0.31 | $3.7 \times 10^5$ |
| 36 | 0.31 | $7.9 \times 10^6$ |
| 42 | 0.34 | $4.9 \times 10^7$ |
| 48 | 0.32 | $2.3 \times 10^8$ |

Example 6
Production of Spores of Trichoderma Species in 50 Liter Pilot Germentor Using FM1 Medium with Higher Concentration of Ingredients.

Spores of Trichoderma species raised in Roux bottles containing solid FM1 medium of the composition as described in Examples 1,3 &5 above were eluted in Tween 80 (0.02% in water) solution as described in examples 1,3 and 5 above. 50 liters of FM1 medium with following ingredients Molasses 20 (g/l), Corn Steep Liquor (CSL) 25.00 (g/l), Sodium chloride 15.00 (g/l), $CaSO_4$ 0.500 (g/l), $KH_2PO_4$ 0.01 (g/l), $MgSO_4.7\ H_2O$ 0.01 (g/l), $CuSO_4$ 0.0050 (g/l), $FeSO_4$ 0.005 (g/l) without agar, along with 15–25 ml of silicon oil as antifoam (the amount of silicon oil varied depending upon development of foam during fermentation) was sterilised in-situ in the 100 l fermentor (Andel, India) at 121° C./15 psig for 15 min. The medium on cooling was inoculated with 450–550 ml of spore suspension in Tween 80 solution with the final spores concentration of $1\times10^6$/ml.

The fermentor was set with the following parameters:

| | |
|---|---|
| Agitation | = 250 rpm (revolutions per min.) |
| Aeration rate | = 0.5 vvm (volume per volume per min.) |
| Temperature | = 29° C. ± 1 |
| Pressure | = 1.2 psig (pounds per square inch × g) |

The fermentation was continued for 48 hours until the spore concentration of $2.3\times10^8$ was achieved (Table 6). Periodic sampling for spore counting was carried out at regular intervals of time as shown in the Table 6.

TABLE 6

Growth and sporulation of Trichoderma species 50 L fermentor using FM1 medium with higher concentration of ingredients.

| Fermentation Period (h) | Dry biomass (g/l) | Spore count/ml |
|---|---|---|
| 0 | 0.02 | $1.0 \times 10^6$ |
| 12 | 0.26 | — |
| 24 | 0.48 | $2.5 \times 10^5$ |
| 30 | 0.38 | $3.9 \times 10^5$ |
| 36 | 0.39 | $8.2 \times 10^6$ |
| 42 | 0.35 | $5.0 \times 10^7$ |
| 48 | 0.30 | $2.7 \times 10^8$ |

Perusal of the data show that the novel medium (FM1) with lower concentrations of ingredients is more economical and has the same spore concentration/ml and incubation period as the FM1 medium with higher concentration of ingredients.

Further the FM1 medium is far superior than the conventional medium (Molasses-yeast extract medium containing Molasses 7.50 (g/l), Glycerin 7.50 (g/l), Sodium Chloride 10.00 (g/l), Yeast Extract 5.00 (g/l), $CaSO_4$ 0.25 (g/l), $KH_2PO_4$ 0.006 (g/l), $MgSO_4.7\ H_2O$ 0.005 (g/l), $CuSO_4$ 0.001 (g/l), and Trace Elements 0.0016 (g/l) when spore concentration/ml and incubation period is taken into consideration.

ADVANTAGES OF THE INSTANT APPLICATION

1. The composition of instant application facilitates early and profuse sporulation.
2. The said composition shows about 100-fold increase in spore count within 48 hours of inoculation.
3. The said composition is very economical as compared to other commercially available compositions for similar use.
4. The method of early and profuse sporulation in fungi facilitates easy availability of scantily sporulating fungi.
5. The said composition and method show significant utility for fungi like Trichoderma species, Aspergillus species, Penicillium species.
6. The major constituents of the medium for the mass production of Trichoderma species, a number of other sporulating ascomycetous fungi such as Aspergillus species, Penicillium species and any other scantily sporulating species of fungi under solid state, surface and submerged fermentation conditions, are inexpensive agro-based industrial by-products like beet-root pulp, wheat bran, corn-steep liquor and molasses.
7. The designed medium FM1 (medium containing Molasses 7.50 (g/l), Corn Steep Liquor (CSL) 20.00 (g/l), Sodium chloride 10.00 (g/l), $CaSO_4$ 0.2500 (g/l), $KH_2PO_4$ 0.0060 (g/l), $MgSO_4.7\ H_2O$ 0.0050 (g/l), $CuSO_4$ 0.0010

(g/l), FeSO$_4$ 0.0016 (g/l) is not only inexpensive but results in profuse sporulation of the order of 200–300 million coniodiospores (2–3×10$^8$ spores/ml) of Trichoderma species, a number of other sporulating ascomycetous fungi such as Aspergillus species, Penicillium species and any other scantily sporulating species of fungi under solid state, surface and submerged fermentation conditions.

8. This novel medium (FM1) reduces fermentation period from 72 hrs in conventional medium to 48 hrs for sporulation. Moreover spore count (3.0×10$^8$) is achieved in this novel medium which is 100 times from the initial inoculum (4–5×10$^6$) in 48 hrs whereas in case of conventional medium (Molasses-yeast) it is less than 10 times (1.05×10$^7$) in 72 hrs. Besides, number of chlamydospores in conventional medium (Molasses-yeast) is much higher as compared to the novel medium (FM1) at any fixed time internal.

9. The spores of this biocontrol agent can be directly blended with the carrier agent without any further processing and used directly in the fields.

What is claimed is:

1. A composition useful for early and profuse sporulation in fungi, said composition comprising molasses ranging between 5–20 g/L, Corn Steep Liquor (CSL) ranging between 10–25 g/L, Sodium chloride (NaCl) ranging between 5–15 g/L, calcium sulphate (CaSO$_4$) ranging between 0.1–0.5 g/L, Potassium dihydrogen phosphate (KH$_2$PO$_4$) ranging between 0.001–0.01 g/L, Magnesium sulphate (MgSO$_4$.7H$_2$O) ranging between 0.001–0.01 g/L, Copper sulphate (CuSO$_4$) ranging between 0.001×0.0050 g/L, Ferrous sulphate (FeSO$_4$) ranging between 0.0009–0.005 g/L, an anti-foam agent, and optionally solidifying agent.

2. A composition as claimed in claim 1, wherein said composition show most efficient sporulation with composition comprising molasses about 7.50 g/L, Corn Steep Liquor (CSL) about 20 g/L, Sodium chloride (NaCl) about 10 g/L, calcium sulphate (CaSO$_4$) about 0.25 g/L, Potassium dihydrogen phosphate (KH$_2$PO$_4$) about 0.0060 g/L, Magnesium sulphate (MgSO$_4$.7 H$_2$O) about 0.0050 g/L, Copper sulphate (CuSO$_4$) about 0.0010 g/L, Ferrous sulphate (FeSO$_4$) about 0.0016 g/L, an anti-foam agent, and optionally solidifying agent.

3. A composition as claimed in claim 1, wherein using silicon oil as an anti-foam agent.

4. A composition as claimed in claim 3, wherein silicon oil ranging between 0.1–0.5 ml.

5. A composition as claimed in claim 1, wherein using agar as a solidifying agent.

6. A composition as claimed in claim 5, wherein agar ranging between 5–25 g/L.

7. A composition as claimed in claim 1, wherein said composition is effective with fungi selected from a group comprising Trichoderma species, Aspergillus species, and Penicillium species.

8. A composition as claimed in claim 1, wherein said composition is effective with fungi Trichoderma species.

9. A composition as claimed in claim 1, wherein said composition shows about 100-fold increase in spore count within 48 hours of inoculation.

10. A composition as claimed in claim 1, wherein said composition shows average spore count ranging between 1–5×10$^8$ conidiospores/ml.

11. A composition as claimed in claim 1, wherein said composition shows percentage viability of generated spores ranging between 90 to 100%.

12. A composition as claimed in claim 1, wherein said composition is equally effective with scantily sporulating fungi.

13. A composition as claimed in claim 1, wherein said composition is used for mass production of fungi of biocontrol activity.

14. A composition as claimed in claim 1, wherein said composition is economical as compared to other commercially available compositions for same purpose.

15. A method for early and profuse sporulation in fungi with about 100 fold increase in spore count within 48 hours of inoculation, said method comprising:
    (a) inoculating about one week old spore culture of the fungi in a medium comprising molasses ranging between 5–20 g/L, Corn Steep Liquor (CSL) ranging between 10–25 g/L, Sodium chloride (NaCl) ranging between 5–15 g/L, calcium sulphate (CaSO$_4$) ranging between 0.1–0.5 g/L, Potassium dihydrogen phosphate (KH$_2$PO$_4$) ranging between 0.001–0.01 g/L, Magnesium sulphate (MgSO$_4$.7H$_2$O) ranging between 0.001–0.01 g/L, Copper sulphate (CuSO$_4$) ranging between 0.001–0.0050 g/L, Ferrous sulphate (FeSO$_4$) ranging between 0.0009–0.005 g/L, an anti-foam agent, and optionally solidifying agent,
    (b) fermenting the inoculated culture at temperature about 27–30° C., and
    (c) obtaining large quantity of viable spores.

16. A method as claimed in claim 15, wherein inoculating said culture of step (a) with said spores of final concentration of about 1×10$^6$ conidia/ml.

17. A method as claimed in claim 15, wherein fermentation said culture of step (b) under solid state, surface, or submerged fermentation conditions.

18. A method as claimed in claim 15, wherein said method using agar as a solidifying agent.

19. A method as claimed in claim 18, wherein agar ranging between 5–25 g/L.

20. A method as claimed in claim 15, wherein rotating said inoculated culture in a rotor at rate of about 200 to 400 revolutions/minute.

21. A method as claimed in claim 20, wherein agitating the said culture with said rotor at about 1.5–3.5 c.m. throw.

22. A method as claimed in claim 15, wherein fermenting said culture with aeration rate of about 0.5–1.0 vvm.

23. A method as claimed in claim 15, wherein fermenting said culture with pressure of about 07–1.4 psig.

24. A method as claimed in claim 15, wherein spores of step (c) show viability ranging between 90 to 100%.

25. A method as claimed in claim 15, wherein using said method for mass production of fungi of biocontrol activity.

26. A method as claimed in claim 25, wherein mixing said culture with a carrier in a ratio ranging between 1:2 to 2:1, to develop commercial formulation with biocontrol activity.

27. A method as claimed in claim 25, wherein carrier used is lignite.

28. A method as claimed in claim 15, wherein said method show most efficient sporulation with composition comprising molasses about 7.50 g/L, Corn Steep Liquor (CSL) about 20 g/L, Sodium chloride (NaCl) about 10 g/L, calcium sulphate (CaSO$_4$) about 0.25 g/L, Potassium dihydrogen phosphate (KH$_2$PO$_4$) about 0.0060 g/L, Magnesium sulphate (MgSO$_4$.7 H$_2$O) about 0.0050 g/L, Copper sulphate (CuSO$_4$) about 0.0010 g/L, Ferrous sulphate (FeSO$_4$) about 0.0016 g/L, an anti-foam agent, and optionally solidifying agent.

29. A method as claimed in claim 15, wherein silicon oil is used as an anti-foam agent.

30. A method as claimed in claim 15, wherein silicon oil ranging between 0.1–0.5 ml.

31. A method as claimed in claim 15, wherein said method shows duration of viability of spores of about 10–14 months at temperature of about 4° C. with carriers.

32. A method as claimed in claim 15, wherein said method shows duration of viability of spores of about 4–8 months at temperature of about 30° C. with carriers.

33. A method as claimed in claim 15, wherein fungi are selected from a group comprising Trichoderma species, Aspergillus species, and Penicillium species.

34. A method as claimed in claim 15, wherein fungi used is Trichoderma species.

35. A method as claimed in claim 15, wherein said method shows about 100-fold increase in spore count within 48 hours of inoculation.

36. A method as claimed in claim 15, wherein said method shows average spore count ranging between $1-5\times10^8$ conidiospores/ml.

37. A method as claimed in claim 15, wherein said method is equally effective for scantily sporulating fungi.

* * * * *